(12) United States Patent
Murphy et al.

(10) Patent No.: US 6,541,517 B1
(45) Date of Patent: *Apr. 1, 2003

(54) TREATMENT OF SKIN DISORDERS

(76) Inventors: Donald M. Murphy, 507 Holly Ave., Madison, WI (US) 53711; Edward R. Ahrens, 1910 Jefferson St., Madison, WI (US) 53711-2114

( * ) Notice: Subject to any disclaimer, the term of this patent is extended or adjusted under 35 U.S.C. 154(b) by 0 days.

This patent is subject to a terminal disclaimer.

(21) Appl. No.: 09/627,933

(22) Filed: Jul. 28, 2000

Related U.S. Application Data

(63) Continuation-in-part of application No. 09/389,837, filed on Sep. 3, 1999, now Pat. No. 6,117,904.

(51) Int. Cl.⁷ .............................................. A61K 31/225
(52) U.S. Cl. ................................................... 514/547
(58) Field of Search .................... 514/547, 11, 169, 514/724

(56) References Cited

U.S. PATENT DOCUMENTS

| | | | |
|---|---|---|---|
| 3,070,497 A | 12/1962 | Knight | |
| 3,091,241 A | 5/1963 | Kellett | |
| 3,975,515 A | 8/1976 | Wajaroff et al. | |
| 3,998,966 A | 12/1976 | Fried et al. | |
| 4,055,653 A | 10/1977 | Offermans et al. | |
| 4,061,753 A | 12/1977 | Bodor et al. | |
| 4,172,149 A | * 10/1979 | Pinto et al. | 514/547 |
| 4,218,447 A | 8/1980 | Isaac et al. | |
| 4,543,360 A | 9/1985 | von Angerer et al. | |
| 4,556,560 A | * 12/1985 | Buckingham | 424/641 |
| 4,734,434 A | 3/1988 | Procaccini et al. | |
| 4,824,865 A | 4/1989 | Bowser et al. | |
| 4,847,297 A | 7/1989 | Chandra | |
| 4,895,727 A | * 1/1990 | Allen | 424/642 |
| 5,061,700 A | 10/1991 | Dow et al. | |
| 5,098,717 A | 3/1992 | Blackman | |
| 5,576,346 A | 11/1996 | Clemente et al. | |
| 5,593,682 A | 1/1997 | Papas et al. | |
| 5,602,183 A | 2/1997 | Martin et al. | |
| 5,646,190 A | 7/1997 | Martin | |
| 5,648,380 A | 7/1997 | Martin | |
| 5,663,208 A | 9/1997 | Martin | |
| 5,702,688 A | 12/1997 | Yu et al. | |
| 5,725,875 A | 3/1998 | Noll et al. | |
| 5,747,462 A | 5/1998 | Fuentes | |
| 5,789,399 A | 8/1998 | Strube | |
| 5,798,093 A | 8/1998 | Farrar et al. | |
| 5,863,938 A | 1/1999 | Martin | |
| 5,874,479 A | 2/1999 | Martin | |
| 5,891,463 A | 4/1999 | Bello et al. | |
| 5,945,398 A | 8/1999 | Singh et al. | |
| 5,961,997 A | 10/1999 | Swinehart | |
| 6,159,977 A | * 12/2000 | Reeves | 514/252 |
| 6,160,200 A | * 12/2000 | Ehrnsperger et al. | 604/378 |

FOREIGN PATENT DOCUMENTS

FR  2467598  * 10/1979

OTHER PUBLICATIONS

Ohman H, Vahlquist A. The pH gradient over the stratum corneum differs in X–linked recessive and autosomal dominant ichthyosis: a clue to the molecular origin of the "acid skin mantle"? J Invest Dermatol Oct. 1998; 111(4):674–7.

Faria DT, Shwayder T, Krull EA. Perineal skin injury: extrinsic environmental risk factors. Ostomy Wound Manage Aug. 1996; 42(7):28–30, 32–4, 36–7.

Spiegel, CA. Vaginitis/vaginosis. Clin Lab Med Sep. 1989; 9(3):525–33.

* cited by examiner

*Primary Examiner*—William Jarvis
*Assistant Examiner*—Vickie Kim
(74) *Attorney, Agent, or Firm*—Barnes & Thornburg; Alice O. Martin

(57) ABSTRACT

The present invention provides a method and composition for treating skin disorders, skin pathologies and pruritus, which includes applying a compound of formula (I) in a suitable formulation to the affected area.

7 Claims, No Drawings

TREATMENT OF SKIN DISORDERS

CROSS-REFERENCE TO RELATED APPLICATIONS

This application is a continuation-in-part of patent application Ser. No. 09/389,837 filed Sep. 3, 1999 now U.S. Pat. No. 6,117,904 in the United States Patent and Trademark Office.

STATEMENT REGARDING FEDERALLY SPONSORED RESEARCH OR DEVELOPMENT

Not Applicable

BACKGROUND OF INVENTION

The milieu of the skin is normally of acidic pH, i.e. the stratum corneum layer of the human skin is normally acidic. The stratum corneum is the thin outer cornified lipophilic epidermal layer of the skin, which functions as a barrier to the external environment. It is now generally accepted that this outer layer of the skin has a natural pH in the range of 4.0 to 6.0, normally 5.0. Ten to fifteen micrometers below the stratum corneum, the pH quickly rises to a neutral pH of 7.0.

Within the thin stratum corneum resides a diverse array of hydrolytic, proteolytic, esterifying, and lipid active enzymes which all appear to function optimally in an acidic range of pH 4.5–6.0, which is typical of this layer. Disruption of the pH of this layer by a vast array of etiologies is associated with numerous well-described pathologic entities. In other words, abnormally high pH, or abnormal alkalization, of the skin is often associated with many pathologic dermatological states.

For example, abnormal alkaline surface pH has been noted in atopic dermatitis. Atopic dermatitis is a chronic, itching, superficial inflammation of the skin, frequently associated with related disorders, such as hay fever and asthma. Atopic dermatitis may begin in the first few months of life, with red, weeping, crusted lesions on the face, scalp, diaper area and extremities. In older children or adults, it may be more localized and chronic. Although the dermatitis often improves by age 3 or 4, exacerbations are common during childhood, adolescents or adulthood. Itching is a constant feature, and consequent scratching and rubbing lead to an itch-scratch-rash-itch cycle.

Another pathology generally associated with abnormally high alkalinity of the skin is ichthyosis. Ichthyosis is a symptom in several rare hereditary syndromes and in several systematic disorders. It usually occurs in the lower legs of middle aged or older patients, most often in cold weather and in patients who bathe frequently. Mild to moderate itching may exist in an associated dermatitis due to detergents or other irritants. Xeroderma is the mildest form of ichthyosis.

Another example is seborrheic dermatitis. Seborrheic dermatitis is an inflammatory scaling disease of the scalp, face and occasionally more generalized areas. Onset in adults is gradual, and the dermatitis usually is apparent only as dry or greasy diffused scaling of the scalp (dandruff) with variable itching. In severe disease, yellow-red scaling papules appear along the hairline, behind the ears, and external auditory canals, on the eyebrows, on the bridge of the nose, the nasolabial folds, and over the sternum. Dry yellow crusting and conjunctival irritation may also be present. Neonates under one month old may develop seborrheic dermatitis, with thick, yellow, crusted scalp lesions, fissuring and yellow scaling behind the ears and red facial papules. Newborns may also have an associated stubborn diaper rash, while older children may develop thick, tenacious, scaly plaques in the scalp that may measure 1 to 2 centimeters in diameter. Very rarely, in infants or adults, the condition may become generalized.

Contact dermatitis, another example of a skin disorder associated with abnormally basic skin, is characterized as an acute or chronic inflammation, produced by substance contact with the skin. Contact dermatitis may be caused by marginal irritants such as soap, detergents, acetone or even water. It may take several days of exposure to cause clinically recognizable changes. Strong irritants, for example, acids and alkalines, cause observable changes within a few minutes. More specifically, allergic contact dermatitis is a delayed hypersensitivity reaction. It takes between 6 and 10 days to years for individual to become sensitized. Often times, ingredients in topical drugs constitute a major cause of allergic contact dermatitis. Other commonly implicated substances include plants, many potential sensitisers used in the manufacture of shoes and clothing, p-phenylenediamine and other dyes and cosmetics. Contact dermatitis ranges from redness to severe swelling and itching. Any exposed skin surface in contact with the sensitizing or irritating substance may be involved.

Pemphigus is an uncommon, potentially fatal, autoimmune skin disorder characterized by bullae on apparently healthy skin and mucus membranes that has been demonstrated to have an abnormally high pH. The primary lesions associated with pemphigus often occur first in the mouth, where they soon rupture and remain as chronic, often painful, erosions for variable periods of time before the skin is affected. On the skin, the bullae typically arise from normal appearing skin to leave a raw, denuded area and crusting when they rupture later.

Dermatitis herpetiformis is a chronic eruption characterized by clusters of intensely pruritic vesicles, papules and urticaria-like lesions. With this dermatitis, itching and burning are severe, and scratching often obscures the primary lesions. This form of dermatitis is also associated with abnormally alkaline skin.

Psoriasis is a common, chronic, recurrent disease characterized by dry, well-circumscribed, silvery, scaling papules and plaques of various sizes that is associated with high alkaline skin surface conditions. Psoriasis varies in severity from one or two lesions to a widespread dermatitis with disabling arthritis or exfoliation. It is generally caused by increased epidermal cell proliferation from abnormally alkaline stratum corneum. Psoriasis characteristically involves the scalp, the extensor surfaces of the extremities, particularly at elbows and knees and the back. The nails, eye brows and other regions may also be affected. Occasionally the disease is generalized.

Candidiasis, or yeast infections, may also be related to an abnormally high pH in the skin or mucous membranes. The symptoms of candidiasis vary from the site of the infection. However, symptoms usually include itchiness and inflammation.

Other skin disorders or pathologies that may be linked with an abnormally basic stratum corneum are acne, dermatophytosis, diaper rash, eczema and skin damage from a variety of causes including wounds, burns and fecal and urinary incontinence. In addition, a more alkaline surface pH has been shown to promote Staphylococcal skin colonization and the invasion of Nector americanus, i.e. human hookworm. Alopecia, or baldness, may also result from abnormal alkaline surface skin pH.

Many of these skin disorders or pathologies are accompanied by pruritus, a condition involving localized or general itching. Although usually occurring in the skin, pruritus can also occur in non-cutaneous sites such as mucous membranes. A variety of causes for the condition of pruritus are known including external and endogenous causes, localized skin disorders and systemic diseases. As previously discussed, many systemic and skin diseases are accompanied by persistent or recurrent itch attacks. Itch can also be produced by a variety of chemical, mechanical, thermal and electrical stimuli.

Research into the etiology of and treatment of many skin pathologies including pruritis has been limited both by the lack of animal models and by patient populations that at present would not support the perceived research and development and clinical testing costs. Treatment involves diagnosis of the underlying condition that causes pruritus and these skin disorders and pathologies and intervening therapeutically to alleviate these conditions. For example, developments leading to drugs to threat these conditions have been, for the most part, a bonus of anti-inflammatory drugs. Such treatments are not considered to be direct treatments of these conditions and are of limited efficacy, only occasionally and indirectly relieving the itching. In many cases, however, either the underlying cause for the condition cannot be determined or cannot be eliminated. In such cases, the direct treatment of the pruritic condition or the accompanying skin disorder is required.

Generally, options for effectively treating these disorders are limited. Currently available treatment modalities for these pathologies include nonspecific topical agents such as emollients and counterirritants, topical and oral drugs such as steroids, local anesthetics and antihistamines, and physical modalities such as ultraviolet phototherapy and thermal stimulation. Some of these treatments are effective in pruritic conditions of a particular etiology, while others may show general but nonspecific benefit. It is known that many corticosteroids, e.g., hydrocortisone, fluocinide, betamethasone valerate, fluocinolene acetonide, triamcinolone acetonide and others, have antiprutitic properties and may be effective in treating some skin disorders. However, prolonged use of such corticosteroids is associated with both cutaneous and systemic toxic side effects (e.g., fluid and electrolyte disturbances, impaired wound healing, musculoskeletal, gastrointestinal, neurological and endocrine disturbances) and their widespread use is limited without medical supervision. Selenium sulfide, sulfur and salicylic acid or tar shampoo have also been employed to treat these skin conditions. In any event, remission of the pathology or pruritus is often slow and frequently incomplete.

Nonspecific topical preparations can act as moisturizing lotions or creams or as oil-based ointments that are occlusive and serve to soften dry skin as well as provide a protective layer. While such preparations may have valuable moisturizing and skin softening properties, they also possess undesirable effects in that they generally impart to the skin an uncomfortable feeling of warmth in addition to a sticky, oily, greasy or waxy feel. More importantly, these materials alone have little effect, if any, on reducing itching.

Topical formulations containing pharmacologically active agents are often useful in particular conditions but many may not be generally useful in all conditions. For example, topical corticosteroids are not indicated for symptomatic treatment unless a steroid responsive disorder is diagnosed.

Thus, there is a continuing need for development of new and improved, nontoxic antipruritic and pH-adjusting agents that are effective in treating and alleviating skin disorders, pathologies and pruritus resulting from a wide variety of causes or causes different than those that can be treated by currently available agents.

BRIEF SUMMARY OF THE INVENTION

The present invention provides a method of treating skin pathologies, disorders and pruritus which includes topically applying a fatty acid esterified with glycerol (or another suitable alcohol) in combination with a dermatologically acceptable vehicle to adjust, regulate or control the skin pH. Examples of suitable fatty acids, as defined herein, include, but are not limited to, acetic acid, propionic acid, butyric acid, valeric acid, caproic acid, etc. The compounds of formula (I), described hereinafter, are examples of suitable fatty acids esterified with glycerol that can be applied to the skin to adjust pH and treat the various skin disorders described above. For example, it has been found that the esters in accordance with the present invention can be applied topically at affected sites and are surprisingly therapeutically effective such that the pruritus is rapidly and completely relieved.

The invention provides a simple, safe and effective way to control skin pH. By normalizing abnormally alkaline skin, i.e. returning the stratum corneum to a more typical acid milieu, many of the skin disorders and pathologies listed above can be treated. Triacetin is one example of a glyceryl fatty acid ester. When applied to abnormally alkaline skin, triacetin is enzymatically hydrolyzed in the alkaline milieu found therein to form glycerol and acetic acid. The acetate ion is a two-carbon moiety that contributes to fatty acid synthesis and ultimately to tissue healing and repair. In other words, the application of triacetin and the other esters provide a safe way to apply an acid to normalize the pH of the skin, and return it to its more natural acid milieu. This results in the normalization of the pH in the stratum corneum and subsequent skin healing. As the skin pH returns to its normal acidic pH, the cleavage of triacetin is halted leading to a simple control mechanism.

The compound of formula (I) is suitably the compound of formula (II) described hereinafter, which is glyceryl triacetate or 1, 2, 3 propanetriol triacetate or, commonly, triacetin. It is again, noted however, that any of the esters described herein that is capable of adjusting the pH of the skin will suffice. Triacetin has been used as a pharmaceutical plasticizer (U.S. Pharmacopoeia National Formulary 1075–76, 1492 (1985)), as an antifungal drug and a fixative in perfumery (see, The Merck Index ($12^{th}$ ed.) p. 1636 (1996); U.S. Pat. No. 3,070,497 issued to Knight), listed as one of many general pharmaceutical carriers/diluents for primarily systemic administration of specific compounds (see, e.g., U.S. Pat. No. 4,543,360 issued to von Angerer et al.; U.S. Pat. No. 4,218,447 issued to Isaac et al.; U.S. Pat. No. 4,055,653 issued to Offermanns et al.; U.S. Pat. No. 4,847,297 issued to Chandra; U.S. Pat. No. 5,061,700 issued to Dow et al.), as an alkalinity reducing agent in permanent waving treatments for hair (see, e.g., U.S. Pat. No. 3,975,515 issued to Wajaroff et al.), and as an ingredient in a vaginal tampon (see, U.S. Pat. No. 3,091,241 issued to Kellett). It is noted that despite disclosure that triacetin is a general antifungal agent, a U.S. Food & Drug Administration Over-the-Counter (OTC) Drug Review Panel has concluded that there is no evidence that triacetin is effective in any fungal disease other than the soggy toeweb form of athlete's foot. The OTC panel also concluded that triacetin was safe for topical use (see, Federal Register, vol. 47, 12553 (Mar. 23, 1982)). It has not heretofore been known that triacetin, the compounds of formula (I) and other esterified fatty acids can be effectively used in the treatment of pruritic conditions and other skin disorders related to pH imbalance.

The foregoing and other advantages of the present invention are realized in one aspect thereof in a method of treating pruritus, skin disorders and skin pathologies which comprises applying a compound of formula (I) in an inert vehicle to the affected area to treat the related skin disorder.

In another aspect, the invention provides a method of treating skin disorders, skin pathologies and pruritus which includes applying a composition to the pathologically or pruritically affected area, which composition essentially consists of a pH modifying substance, self regulating at the molecular level, that stabilizes the desirable healthy skin pH, namely a glyceryl fatty acid ester, e.g. a compound of formula (I).

In a further aspect, the invention provides a topical anti-pathologic or antipruritic composition consisting of 5–100%, preferably 5–50%, by weight of a glyceryl fatty acid ester, e.g. a compound of formula (I), and 0%–95% by weight a dermatologically acceptable vehicle. The glyceryl fatty acid ester in accordance with the present invention acts as an essential active ingredient for normalizing the skin pH to treat the skin pathology.

In yet a further aspect, the invention provides a prodrug composition for treating skin disorders, skin pathologies and pruritus which consists essentially of 5–100% by weight of a glyceryl fatty acid ester, e.g. a compound of formula (I), and 0%–95% by weight a dermatologically acceptable vehicle.

DETAILED DESCRIPTION OF THE INVENTION

The present invention relates to a method of treating pruritus and other skin disorders which is highly effective in providing rapid and sustained relief. Accordingly, the present invention will now be described in detail with respect to such endeavors. Those skilled in the art will appreciate that such a description of the invention is meant to be exemplary only and should not be viewed as limitative of the full scope thereof.

The term "pruritus" is meant to refer to itching which can range from a mild sensation to an intense sensation of itching pain. The itching may accompany primary skin disease or may be a symptom of systemic disease—sometimes the only symptom. Skin diseases in which itching can be most severe include, among others, scabies, pediculosis, insect bites, urticaria, atopic dermatitis, contact dermatitis, lichen planus, miliaria and dermatitis herpetiformis. Also, dry skin (especially in the elderly) is often a cause of severe generalized itching.

The terms "skin disorder" and "skin pathology" are meant to refer to and include skin conditions such as atopic dermatitis, ichthyosis, xeroderma, seborrheic dermatitis, allergic contact dermatitis, alopecia, pemphigus, dermatitis herpetiformis, psoriasis, candidiasis, acne, dermatophytosis, diaper rash, cradle cap, eczema, hookworm and skin damage from, e.g., wounds, burns, and fecal and urinary incontinence. These examples are purely illustrative and are not meant to limit the scope of the invention.

The term "compound of formula (I)" is meant to refer to the following

wherein $R_1$, $R_2$ and $R_3$ are each independently RCOO— or H provided that $R_1$, $R_2$ and $R_3$ are not all H. With regard to RCOO—, R is a saturated or unsaturated, straight or cyclic, $C_2$–$C_{22}$ alkyl group. For saturated fatty acids, R is suitably represented by $C_nH_{2n+1}$, such as $CH_3COO—$, $CH_3CH_2COO—$ or $CH_3(CH_2)_2COO—$, etc. For unsaturated fatty acids, R is suitably represented by the formula $C_nH_{2n-m}$, wherein n is an integer from 1 to 23, and m is an odd integer from 1 to 7, provided that m is less than 2n. Examples of suitable unsaturated fatty acids include, but are not limited to oleic acid, linolenic acid, linoleic acid and arachidonic acid. Positional and geometric isomers of unsaturated fatty acids are considered within the scope of formula I.

The term "fatty acid" as used herein is meant to refer to saturated and unsaturated acids composed of a chain of alkyl groups and characterized by a terminal carboxyl group —COOH. Fatty acids may contain from 2 to 24 carbon groups. The term "fatty acid" includes, but is not limited to, acetic acid, butyric acid, propionic acid, valeric acid and caproic acid. The compound of formula (I) shows a variety of both saturated and unsaturated fatty acids.

The term "glyceryl fatty acid ester" is meant to refer to a fatty acid, as described above, esterified with glycerol.

The present invention is also suitably used for the relief of epidermal or dermal itching associated with any condition such as a systemic disease or allergy that affect epidermal and/or dermal nerve endings, an injury resulting in localized trauma affecting the epidermal or dermal nerve endings, or localized dermatitis. In a preferred method, the invention includes a method of relief of pruritic symptoms associated with dermatitis including actinic dermatitis, contact dermatitis such as an allergic dermatitis or contact dermatitis caused by irritating substances of plant, animal, mineral or synthetic origin.

The method of the present invention includes applying to an affected area an effective amount of a glyceryl fatty acid ester, for example, the compound of formula (I):

wherein $R_1$, $R_2$ and $R_3$ are each independently RCOO— or H provided that $R_1$, $R_2$ and $R_3$ are not all H and R is a saturated or unsaturated, straight or cyclic, $C_2$–$C_{22}$ alkyl group. For saturated fatty acids, R is suitably represented by $C_nH_{2n+1}$. For example, When n is 1, $R_1$, $R_2$ and $R_3$ are each independently $CH_3COO—$ or H. When $R_1$ is $CH_3COO—$ and $R_2$ and $R_3$ are H, the compound of formula (I) is glycerol monoacetate or monacetin. When $R_1$ and $R_2$ are $CH_3COO—$ and $R_3$ is H, the compound of formula (I) is glycerol diacetate or diacetin. When $R_1$, $R_2$ and $R_3$ are all $CH_3COO—$, the compound of formula (I) is glycerol triacetate or triacetin. Triacetin or 1,2,3-propanetriol triacetate or glycerol triacetate is given by formula (II):

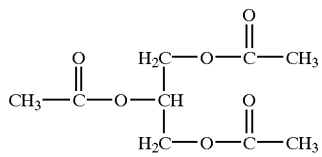

Besides triacetin, diacetin and monoacetin, other esters are suitable for adjusting skin pH, thereby treating and alleviating certain skin disorders. Other suitable fatty acids that can be esterified to glycerol include, but are not limited to, acetic acid, propionic acid, butyric acid, valeric acid and caproic acid. Again, these compounds are illustrated again by formula (I),

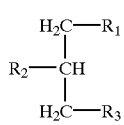

wherein $R_1$, $R_2$ and $R_3$ are each independently RCOO— or H provided that $R_1$, $R_2$ and $R_3$ are not all H. With regard to RCOO—, R is a saturated or unsaturated, straight or cyclic, $C_2$–$C_{22}$ alkyl group. For saturated fatty acids, R is suitably represented by $C_nH_{2n+1}$. RCOO— is suitably, for example, $CH_3COO$—, $CH_3CH_2COO$— or $CH_3(CH_2)_2COO$—, etc. For unsaturated fatty acids, R is suitably represented by the formula $C_nH_{2n-m}$ wherein n is an integer from 1 to 23, and m, which is the number of double bonds in R, is an odd integer from 1 to 7, provided that m is less than 2n.

Compounds of formula (I) and other esters formed from the esterification of an acid with glycerol have not previously been recognized as undergoing biotransformation to exhibit a desired pharmacological effect i.e., they are, in effect, prodrugs. These compounds are readily broken down by enzymes, namely esterases, present in or on the skin, in mucus membranes and in body fluids, into glycerol (a skin protectant) and a fatty acid, which is ionized to an anion and a hydrogen ion. When $R_1$, $R_2$ and/or $R_3$ are $CH_3COO$—, for example, the ester is broken down by esterase to glycerol, acetate ion and hydrogen ion. Again, many skin disorders and pathologies are caused by abnormally alkaline conditions in skin and membranes. The hydrogen ions tend to normalize and return the skin pH to a more normal acidic milieu. The action of the esterases continues until the pH of the environment is changed to about 4.0 to 6.0 which is the normal range for healthy skin. At this pH level, the activity of the esterases is inhibited until the pH rises again to a level where the esterases again become active. Also present in the skin and other bodily environments is a protease enzyme that signals the itch sensation. This protease is also pH sensitive in the same range, and it is believed that pH balance that is possible with application of compounds of formula (I) provides a dramatic and surprising effect on pruritus.

The compounds of formula (I) are commercially available. For example, triacetin is commercially available in USP grade from Eastman Chemical Company, Kingsport, Tenn. It is a colorless, somewhat oily liquid with a slight fatty odor with a density at 25° C. of 1.156 g/mL. It is prepared by acetylation of glycerol. Triacetin, diacetin and monoacetin are miscible in water, alcohol, ether and chloroform.

For topical application, suitable viscous, semi-solid or solid forms can be employed which include a carrier compatible with topical application. Suitable formulations include, but are not limited to, solutions, suspensions, emulsions, creams, ointments, powders, liniments, salves, sprays, aerosols and gels. Preferably, compounds of formula (I), e.g., triacetin, are formulated as an ointment in which the vehicle is Aquaphor®, commercially available from Beiersdorf Inc., Norwalk, Conn., US. Aquaphor® is a composition of petrolatum, mineral oil, mineral wax and wool wax alcohol. Compounds of formula (I) are also suitably formulated as up to a 6% solution in water, and a 25% solution in 50% alcohol, suitably isopropyl alcohol.

Optionally, the skin treating compositions of the present invention may suitably include auxiliary agents such as plasticizing agents, preservatives, stabilizers, demulsifiers, wetting agents, opacifiers, surfactants, fragrances, sunscreens, antibiotics, insect repellants, preservatives, emollients, humectants, emulsifiers, thickeners, moisturizers, astringents, deodorants as well as other compatible materials which may be desired to enhance the properties of the compositions.

Other suitable emollient vehicles include hydrocarbon oils and waxes and volatile silicone fluids such a low molecular weight dimethyl siloxanes.

For topical treatment of skin disorders associated with alkaline skin pH, the concentration of the glyceryl ester in accordance with the present invention in a locally applied composition is about 5% to about 100% by weight, preferably about 5% to about 50% by weight, i.e., about 0.05 g/g to 0.5 g/g of composition, and most preferably, the concentration is about 20% by weight. An ester concentration of 55–100% is also acceptable.

These compounds, particularly, triacetin, have been found of value in the relief and treatment of pruritus due to leukoclastic vasculitis, macular lesion from drug allergies, skin conditions associated with renal disease, dry skin, dandruff, anal itch, poison ivy, poison oak, poison sumac, insect bites, vaginitis, bladder infection, diaper rash, cradle cap and eczema. Administering these compounds as a vaginal cream can normalize vaginal acidity. As a result, this controls and help maintain the normal healthy vaginal flora, thereby preventing bacteria and viruses that cause sexually transmitted diseases from becoming established. These compounds of formula (I) are also of value in treating psoriatic lesions. Triacetin has been found to improve psoriatic lesions, applied as a topical, episodic treatment for psoriasis. As previously discussed, these compounds can also treat and provide relief for other skin disorders and pathologies, including atopic dermatitis, ichthyosis, xeroderma, seborrheic dermatitis, allergic contact dermatitis, alopecia, pemphigus, dermatitis herpetiformis, psoriasis, candidiasis, acne, dermatophytosis and other skin damage caused from a variety of wounds, burns and incontinence.

The skin treating compositions of the present invention when applied to the skin, e.g., up to four times per day as needed, provide reduction in and relief from itching within about 24–36 hours, and relief may even be evident after the first dose. For treatment of psoriasis, improvement is often seen within a day, with complete healing occurring within about 5 to 7 days.

The skin treating composition of the present invention is suitably formulated by simply mixing the compounds of formula (I) with the vehicle at room temperature. The composition is formulated to provide delivery of the antipruritic compound at a suitable rate and concentration. The composition may be in the form of any formulation that provides the compound as bioavailable to esterase action.

The following examples are intended to illustrate, but not limit, the scope of the invention. All parts and percentages in the examples are on a weight basis unless otherwise stated.

MEDICAMENT PREPARATIONS

EXAMPLE 1

An ointment was prepared by mixing 20 g of triacetin in 80 g of Aquaphor® to yield a 20% by weight composition.

EXAMPLE 2

A topical cream is prepared by dissolving 20 g of triacetin in 40 g of mineral oil and 20 g of self-emulsifying beeswax. The mixture is heated to liquefy. After the addition of 20 mL of hot water, the mixture is mixed well. The resulting cream contains approximately 20 g of triacetin per 100 gram of cream.

EXAMPLE 3

A dermatological lotion is prepared by dissolving 20 g of triacetin in 80 g of dry propylene glycol. The resulting lotion contains about 20 g of triacetin per 100 g of lotion.

EXAMPLE 4

An ointment is prepared according to Example 1 by dissolving monacetin.

EXAMPLE 5

An ointment is prepared according to Example 1 by dissolving diacetin.

DERMATOLOGICAL TESTING

EXAMPLE 6

Treatment of Pruritus

Compositions of triacetin were evaluated for therapeutic efficacy of the composition in the topical treatment of pruritus. The skin treating composition evaluated was the ointment composition prepared in Example 1. The patients were treated on an outpatient basis. The patients were instructed to apply the composition up to four times per day as needed.

More than 100 subjects who presented with pruritic conditions applied the ointment to the pruritic area up to 4 times per day as needed. Patients were asked to note the time within which itching was relieved and when the symptoms wholly disappeared and reported same to a physician. 90% of the patients reported relief from itching within 24–36 hours, and 75% reported that within about 48 hours of additional treatment, the symptoms essentially disappeared.

EXAMPLE 7

Treatment of Psoriasis

Eight patients who presented with psoriatic lesions were treated with the ointment of Example 1 on an outpatient basis. The ointment of Example 1 was applied to the psoriatic lesions up to four times per day. All patients reported to a physician improvement of the lesions within about a day of application, and healing within about 5–7 days.

In summary, the present invention provides a method and composition for treating a variety of skin disorders including pruritus and psoriasis, which includes applying glyceryl fatty acid esters, including the compounds of formula (I) in a suitable formulation to the affected area. These compounds can also be formulated as a vaginal cream that may be of value for controlling vaginal pH, which may prevent the establishment of viruses such as HIV.

Many variations will suggest themselves to those skilled in the art in light of the detailed description. All such modifications and variations are within the full intended scope of the appended claims.

What is claimed is:

1. A method of normalizing alkaline pH of a pathologically affected area of the skin a human or other mammal, said method comprising:
    (a) obtaining a composition consisting essentially of a glyceryl fatty acid ester and an inert vehicle; and
    (b) applying to the affected area of the skin an amount of the composition wherein the amount is sufficient to adjust the existing pH to a pH of about 4–6.

2. The method of claim 1, wherein the glyceryl fatty acid ester is a compound of formula (I),

wherein $R_1$, $R_2$, and $R_3$ are each independently RCOO— or H, provided that $R_1$, $R_2$, and $R_3$ are not all H, and R is a saturated or unsaturated, straight or cyclic, $C_2$–$C_{22}$ alkyl group.

3. The method of claim 2, wherein the saturated alkyl group is represented by $C_nH_{2n+1}$, and n is an integer from 1 to 23.

4. The method of claim 2, wherein the unsaturated alkyl group is represented by $C_nH_{2n-m}$, and n is an integer from 1 to 23 and m is an odd integer from 1 to 7, provided that m is less than 2n.

5. The method of claim 3, wherein n is 1.

6. The method of claim 5, wherein the compound of formula (I) is triacetin.

7. The method of claim 1, wherein the pathologically affected area of the skin is selected from the group consisting of psoriasis, a psoriatic lesion, atopic dermatitis, ichthyosis, xerodenna, allergic contact dermatitis, alopecia, pemphigus, dermatitis herpetiforis, candidiasis, acne, deniatophytosis, diaper rash, eczema and skin damage caused by wounds, burns or incontinence.

* * * * *